United States Patent
Ford

(10) Patent No.: US 9,339,491 B2
(45) Date of Patent: May 17, 2016

(54) USE OF A PYRAZOLE DERIVATIVE IN THE TREATMENT OF ACUTE EXACERBATIONS OF CHRONIC OBSTRUCTIVE PULMONARY DISEASE

(71) Applicant: Mereo BioPharma 1 Limited, London (GB)

(72) Inventor: Paul Andrew Ford, Horsham (GB)

(73) Assignee: Mereo BioPharma 1 Limited, London (GB)

( * ) Notice: Subject to any disclaimer, the term of this patent is extended or adjusted under 35 U.S.C. 154(b) by 0 days.

(21) Appl. No.: 14/386,174

(22) PCT Filed: Mar. 19, 2013

(86) PCT No.: PCT/EP2013/055730
§ 371 (c)(1),
(2) Date: Sep. 18, 2014

(87) PCT Pub. No.: WO2013/139809
PCT Pub. Date: Sep. 26, 2013

(65) Prior Publication Data
US 2015/0031736 A1 Jan. 29, 2015

Related U.S. Application Data

(60) Provisional application No. 61/613,187, filed on Mar. 20, 2012.

(51) Int. Cl.
*A61K 31/415* (2006.01)
(52) U.S. Cl.
CPC .................................. *A61K 31/415* (2013.01)
(58) Field of Classification Search
CPC .................................................. A61K 31/314
See application file for complete search history.

(56) References Cited

FOREIGN PATENT DOCUMENTS

| GB | WO 2007096151 A2 * | 8/2007 | ........... A61K 31/415 |
|---|---|---|---|
| WO | 2005009973 A1 | 2/2005 | |
| WO | 2007096151 A2 | 8/2007 | |

OTHER PUBLICATIONS

Derivative; Merriam Webster; http://www.merriam-webster.com/dictionary/derivative; accessec Jan. 15, 2016.*
Esters; IUPAC Goldbook; http://goldbook.iupac.org/E02219.html; accessed Jan. 15, 2015.*
Acetals; http://goldbook.iupac.org/A00062.html; accessed Jan. 15, 2016.*
Ketals; http://goldbook.iupac.org/K03376.html; accessed Jan. 15, 2016.*
Hemiacetals; http://goldbook.iupac.org/H02774.html; accessed Jan. 15, 2016.*
Acid; IUPAC Goldbook; http://goldbook.iupac.org/A00071.html; accessed Jan. 15, 2016.*
Base; IUPAC Goldbook; http://goldbook.iupac.org/A00071.html; accessed Jan. 15, 2016.*
Prodrug; http://dictionary.reference.com/browse/prodrug; accessed Jan. 15, 2016.*
Hemiketals; http://goldbook.iupac.org/H02776.html; accessed Jan. 15, 2016.*
Elssner et al.; "Isolation, Identification, and Synthesis of γ-Butyrobetainyl-CoA and Crotonobetainyl-CoA, Compounds Involved in Carnitine metabolism of *E. coli*"; 2000; Biochemistry; 39: 10761-10769.*
Lomas et al. ; "An Oral Inhibitor of p38 MAP Kinase Reduces Plasma Fibrinogen in Patients With Chronic Obstructive Pulmonary Disease"; J Clin Pharmacol.; Mar. 2012; 52(3): 416-24. doi: 10.1177/0091270010397050. Epub Nov. 16, 2011.*
Chopra et al.; "Therapeutic potential of inhaled p38 mitogen-activated protein kinase inhibitors for inflammatory pulmonary diseases"; 2008; Expert Opinion on Investigational Drugs; 17(1): 1411-1425.*
Leidy et al in International Society for Pharmacoeconomics and Outcomes Research, vol. 13, No. 8, 2010, pp. 965-975.
Leidy et al in Am. J. Respir. Crit. Care Med. vol. 183, 2011, pp. 323-329.
Celli and Vestbo in Am. J. Respir. Crit. Care Med. vol. 183, 2011, pp. 287-291.
Jones et al in Chest vol. 139, No. 6, 2011, pp. 1388-1394.
Han et al. (1995) Biochim. Biophys. Acta 1265(2-3):224-7.
Jiang et al. (1996) J. Biol. Chem. 271 (30):17920-6.
Wang et al, Effect of sequential treatment with syndrome differentiation on acute exacerbation of chronic obstructive pulmonary disease and AECOPD Risk-Window; study protocol for a randomized placebo-controlled trial, Trials, Biomed Central, London, GB, Apr. 20, 2012, vol. 13, No. 1, p. 40.
Ikeda et al., Pharmacological Treatment in Acute Exacerbations of Chronic Obstructive Pulmonary Disease, Drugs and Aging, ADIS International Ltd., NZ, Jan. 1, 1998, vol. 12, No. 2, pp. 129-137.

\* cited by examiner

*Primary Examiner* — Timothy Thomas
(74) *Attorney, Agent, or Firm* — Wolff IP, a Prof. Corp.; Jessica R. Wolff, Esq.

(57) ABSTRACT

Use of 3-[5-amino-4-(3-cyanobenzoyl)-pyrazol-1-yl]-N-cyclopropyl-4-methylbenzamide or a pharmaceutically acceptable derivative thereof in the manufacture of a medicament for the treatment of acute exacerbations of chronic obstructive pulmonary disease. Treatment may involve a single dose of the active ingredient by oral administration.

11 Claims, No Drawings

USE OF A PYRAZOLE DERIVATIVE IN THE TREATMENT OF ACUTE EXACERBATIONS OF CHRONIC OBSTRUCTIVE PULMONARY DISEASE

FIELD OF THE INVENTION

This invention relates to organic compounds and their use as pharmaceuticals, more specifically, to a novel use of 3-[5-amino-4-(3-cyanobenzoyl)-pyrazol-1-yl]-N-cyclopropyl-4-methylbenzamide or a pharmaceutically acceptable derivative thereof, namely in the treatment of acute exacerbations of chronic obstructive pulmonary disease.

BACKGROUND OF THE INVENTION

International patent application WO 2005/009973 discloses various pyrazole- and midazole-based compounds or pharmaceutically acceptable derivatives thereof that have cytokine inhibitory activity. It discloses such compounds can be used to treat conditions associated with p38 kinases, especially p38α and β kinases, including inter alia asthma, allergies, adult respiratory distress syndrome and chronic obstructive pulmonary disease.

WO 2005/009973 discloses 3-[5-amino-4-(3-cyanobenzoyl)-pyrazol-1-yl]-N-cyclopropyl-4-methylbenzamide as one such novel pyrazole-based p38 kinase inhibitor and describes processes for its preparation.

It has now been found that 3-[5-amino-4-(3-cyanobenzoyl)-pyrazol-1-yl]-N-cyclopropyl-4-methylbenzamide and pharmaceutically acceptable derivatives thereof are useful in treating acute exacerbations of chronic obstruction pulmonary disease. Surprisingly a single dose, for example administered orally, accelerates the recovery to the stable disease state. As such this treatment represents a new and innovative type of treatment that is disease-modifying, at least in the short term, and thereby provides significant benefits over existing maintenance therapies and existing rescue therapies.

SUMMARY OF THE INVENTION

In a first aspect, the present invention relates to the use of 3-[5-amino-4-(3-cyanobenzoyl)-pyrazol-1-yl]-N-cyclopropyl-4-methylbenzamide in the manufacture of a medicament for the treatment of acute exacerbations of chronic obstructive pulmonary disease.

In a second aspect, the present invention relates to 3-[5-amino-4-(3-cyanobenzoyl)-pyrazol-1-yl]-N-cyclopropyl-4-methylbenzamide or a pharmaceutically acceptable derivative thereof for use in the treatment of acute exacerbations of chronic obstructive pulmonary disease.

In a third aspect, the present invention relates to a method for the treatment of acute exacerbations of chronic obstructive pulmonary disease which comprises administering to a subject in need thereof an effective amount of 3-[5-amino-4-(3-cyanobenzoyl)-pyrazol-1-yl]-N-cyclopropyl-4-methylbenzamide or a pharmaceutically acceptable derivative thereof.

In a fourth aspect, the present invention relates to a pharmaceutical composition for oral administration that contains 3-[5-amino-4-(3-cyanobenzoyl)-pyrazol-1-yl]-N-cyclopropyl-4-methylbenzamide or a pharmaceutically acceptable derivative thereof.

TERMS

Unless defined otherwise, all technical and scientific terms used herein have the same meaning as is commonly understood by one of skill in the art to which the invention(s) belong.

Terms used in the specification have the following meanings:

"Chronic obstructive pulmonary disease" or "COPD" as used herein is a common preventable and treatable disease that is characterised by persistent airflow limitation that is usually progressive and associated with an enhanced chronic inflammatory response in the airways and the lung to noxious particles of gases. Characteristic symptoms of the disease include dyspnea, chronic cough and chronic sputum production.

"Acute exacerbations of chronic obstructive pulmonary disease" or "AECOPD" as used herein mean a sudden worsening of any of the symptoms of the chronic obstructive pulmonary disease, typically involving decreased airflow and increased lung hyperinflation versus stable COPD. Acute exacerbations generally have a substantial negative impact on the well-being of patients and typically require the patient to receive urgent medical treatment in a hospital in an attempt to return the patient to the previously stable disease state.

"Pharmaceutically acceptable derivative" as used herein means a derivative of the therapeutically active compound in question that is suitable for use as an active ingredient of a pharmaceutical product.

"Forced Expiratory Volume in One Second" or "$FEV_1$" as used herein is the volume of air that can forcibly be blown out in one second, after full inspiration, which is measured by a spirometer. It is a measure of lung function or performance. Average values for $FEV_1$ in healthy people depend mainly on sex and age. Values of between 80% and 120% of the average value are considered normal.

"BORG Score" as used herein refers to a measurement of dyspnea in accordance with the Borg scale. On that scale 0 represents no breathlessness at all and 10 represents maximum breathlessness.

"EXACT PRO" as used herein refers to a qualitative method used to develop the EXAcerbation of Chronic pulmonary disease Tool (EXACT), a new Patient-Reported Outcome (PRO) instrument for evaluating frequency, severity and duration of exacerbations of chronic obstructive pulmonary disease. The tool and its development is described by Leidy et al in *International Society for Pharmacoeconomics and Outcomes Research*, vol. 13, no. 8, 2010, pages 965-975. The tool and its validation are described by Leidy et al in *Am. J. Respir. Crit. Care Med.* vol. 183, 2011, pages 323-329, by Celli and Vestbo in *Am. J. Respir. Crit. Care Med.* vol. 183, 2011, pages 287-291, and by Jones et al in Chest vol. 139, no. 6, 2011, pages 1388-1394.

"p38α" as used herein refers to the enzyme disclosed in Han et al. (1995) *Biochim. Biophys. Acta* 1265(2-3):224-7.

"p38β" as used herein refers to the enzyme disclosed in Jiang et al. (1996) *J. Biol. Chem.* 271 (30):17920-6.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

The entire disclosure of each United States patent and international patent application mentioned in this patent specification is fully incorporated by reference herein for all purposes.

DETAILED DESCRIPTION OF THE INVENTION

The present invention concerns a novel use of 3-[5-amino-4-(3-cyanobenzoyl)-pyrazol-1-yl]-N-cyclopropyl-4-methylbenzamide or a pharmaceutically acceptable derivative thereof, namely in the treatment of acute exacerbations of chronic obstructive pulmonary disease.

This may also be expressed as: (a) the use of 3-[5-amino-4-(3-cyanobenzoyl)-pyrazol-1-yl]-N-cyclopropyl-4-methyl-benzamide or a pharmaceutically acceptable derivative thereof in the manufacture of a medicament for the treatment of acute exacerbations of chronic obstructive pulmonary disease; (b) 3-[5-amino-4-(3-cyano-benzoyl)-pyrazol-1-yl]-N-cyclopropyl-4-methylbenzamide or a pharmaceutically acceptable derivative thereof for use in the treatment of acute exacerbations of chronic obstructive pulmonary disease; or (c) a method of treating acute exacerbations of chronic obstructive pulmonary disease which comprises administering to a subject in need thereof an effective amount of 3-[5-amino-4-(3-cyanobenzoyl)-pyrazol-1-yl]-N-cyclopropyl-4-methyl-benzamide or a pharmaceutically acceptable derivative thereof.

3-[5-Amino-4-(3-cyanobenzoyl)-pyrazol-1-yl]-N-cyclopropyl-4-methylbenzamide (herein "Compound A") has the following chemical structure:

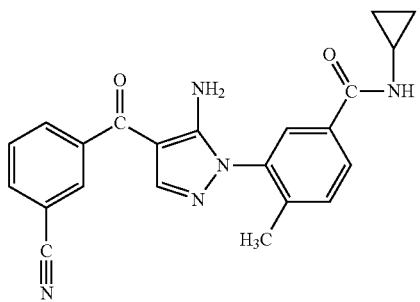 [SMILES: Cc1ccc(C(=O)NC2CC2)cc1-n1ncc(C(=O)c2cccc(C#N)c2)c1N]

International patent application WO 2005/009973 discloses various pyrazole- and imidazole-based compounds or pharmaceutically acceptable derivatives thereof that have cytokine inhibitory activity. These compounds include 3-[5-amino-4-(3-cyanobenzoyl)-pyrazol-1-yl]-N-cyclopropyl-4-methylbenzamide.

WO 2005/009973 discloses the pyrazole- and imidazole-based compounds or pharmaceutically acceptable derivatives thereof can be used to treat conditions associated with p38α and β kinases and to treat p38 kinase-associated conditions including pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid fonnation, scar tissue fonnation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, 5 sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

Chronic obstructive pulmonary disease (COPD) and acute exacerbations of chronic obstructive pulmonary disease (AE-COPD) are distinct indications or at least concern distinct disease states that require different treatment.

COPD is a common preventable and treatable disease that is characterised by persistent airflow limitation that is usually progressive and associated with an enhanced chronic inflammatory response in the airways and the lung to noxious particles of gases. COPD affects more than 80 million people worldwide. It is currently the fourth most frequent cause of death in the world and has been predicted to become the third most frequent cause of death by 2030. Characteristic symptoms of the disease include dyspnea, chronic cough and chronic sputum production. Of these dyspnoea is usually the most prominent and distressing symptom. The main pathophysiological features of COPD are expiratory airflow limitation and air trapping, which manifest as lung hyperinflation and dynamic lung hyperinflation during increased ventilation. This lung hyperinflation contributes to the dyspnoea and resultant activity limitations during stable disease. As the disease progresses, the severity of dyspnoea and other symptoms increases and quality of life for the patient decreases.

Treatment of COPD in its stable chronic disease state typically involves the patient self-administering a long-acting bronchodilator, for example a long-acting $\beta_2$-agonist (LABA) or a long-acting muscarinic antagonist (LAMA) alone or in combination with a corticosteroid (ICS). These compounds are generally formulated for pulmonary administration up to four times a day using one or more inhalation devices. Such treatment is intended to provide a maintenance therapy, relieving symptoms and helping to prevent acute exacerbations.

Patients who have COPD, especially severe COPD, may experience an acute exacerbation i.e. a sudden and serious worsening of their condition that requires hospitalisation to return the patient to a stable condition. Physicians typically treat patients experiencing an acute exacerbation with oral steroids (for example prednisone) and/or antibiotics and/or oxygen but the clinical benefit, especially for oral steroids, is at best marginal. On average a patient will need to spend 8.4 days in hospital to recover to the previous stable disease state, although this varies from country to country due to differences in clinical practice and hospitalisation costs. Sometimes the recovery is not complete. Some acute exacerbations prove fatal.

It has now been found that treating a COPD patient who is experiencing an acute exacerbation with a single dose of Compound A accelerates the recovery time. This reduces the time spent in hospital thus reducing stress for the patient and reducing hospitalisation costs for the patient, insurer, national health system or other relevant payer. Furthermore this treatment may reduce treatment failures, increase returns to baseline, reduce or potentially eliminate steroid treatment and perhaps delay the onset of the next acute exacerbation. As such this treatment represents a new and innovative type of treatment that is disease-modifying, at least in the short term, and thereby provides significant benefits over existing maintenance therapies and existing rescue therapies.

Compound A may be prepared by the processes described in WO 2005/009973, the contents of which is incorporated herein by reference. More specifically, Compound A may be prepared by the processes described in Example 52 or Example 161 of WO 2005/009973.

All stereoisomers of Compound A are contemplated, either in admixture or in pure or substantially pure form. Compound A as used herein embraces all the possible stereo isomers and their mixtures. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization. Compound A may also have prodrug forms. Any compound that will be converted in vivo to provide the bioactive agent is a prodrug. Various forms of prodrugs are well known in the art.

Pharmaceutically acceptable derivatives of Compound A include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, l-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, nitrates, borates, methanesulfonates, benzenesulfonates, toluenesulfonates, salts of mineral acids, such as but not limited to hydrochlorides, hydrobromides, hydroiodides and sulfates; and salts of organic acids, such as but not limited to acetates, trifluoroacetates, oxalates, benzoates, salicylates, maleates, lactates, malates, tartrates, citrates, ascorbates, succinates, butyrates, valerates and fumarates. In addition, zwitterions ("inner salts") may be formed. In certain embodiments, salt forms of the compounds improve the compounds' dissolution rate and oral bioavailability. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

Compound A may be formulated to be administered by any appropriate route, e.g. orally, for example in the form of a tablet or capsule; parenterally, for example intravenously; topically to the skin, for example in the treatment of psoriasis; intranasally, for example in the treatment of hay fever; or by inhalation. Such compositions may be prepared using conventional diluents or excipients and techniques known in the galenic art. Thus oral dosage forms may include tablets and capsules. Compositions for topical administration may take the form of creams, ointments, gels or transdermal delivery systems, e.g. patches. Compositions for inhalation may comprise aerosol or other atomizable formulations or dry powder formulations.

In certain preferred embodiments of the invention there is provided a pharmaceutical composition for oral administration that contains 3-[5-amino-4-(3-cyanobenzoyl)-pyrazol-1-yl]-N-cyclopropyl-4-methylbenzamide or a pharmaceutically acceptable derivative thereof.

Dosages employed in practising the invention will vary depending, for example, on the mode of administration. In certain preferred embodiments of the invention there is provided a pharmaceutical composition for oral administration that contains 50 to 100 mg, for example 60 to 90 mg, including 75 mg of 3-[5-amino-4-(3-cyanobenzoyl)-pyrazol-1-yl]-N-cyclopropyl-4-methylbenzamide or a pharmaceutically acceptable derivative thereof.

Additional embodiments and features are set forth in part in the description that follows, and in part will become apparent to those skilled in the art upon examination of the specification or may be learned by the practice of the invention.

This invention is further illustrated by the following example which should not be construed as limiting.

EXAMPLES

Example 1

An exploratory, randomized, double-blind, placebo controlled, multi-center study to assess the efficacy, safety and tolerability of a single 75 mg dose of 3-[5-amino-4-(3-cyanobenzoyl)-pyrazol-1-yl]-N-cyclopropyl-4-methylbenzamide administered orally to patients who have an acute COPD exacerbation The efficacy, safety and tolerability of a single 75 mg dose of 3-[5-amino-4-(3-cyano-benzoyl)-pyrazol-1-yl]-N-cyclopropyl-4-methylbenzamide (Compound A) administered orally to patients who have an acute COPD exacerbation was conducted.

The study objectives were as follows:
Primary objective: Assess the efficacy of a single 75 mg dose of Compound A in COPD patients presenting with an exacerbation as measured by the improvement in $FEV_1$ over the first 5 days of treatment relative to placebo.
Secondary objectives: Safety and tolerability, patient reported outcomes, and time to next exacerbation.
Study design:
90 patients were randomized 1:1:1 to three treatment arms.
Treatment A (n=15)
=single 75 mg dose of Compound A on day 1+prednisone placebo×10 days Treatment B (n=15)
=single dose of Compound A placebo on day 1+prednisone placebo×10 days
Treatment C (n=15)
=single dose of Compound A placebo on day 1+40 mg oral prednisone placebo×10 days
All treatment arms
=doxycycline 100 mg dose×10 days or a non-macrolide antibiotic concurrent with local prescribing antibiotic guidelines.
Visits at Days 3, 5 and 14 and follow-up visits 30 and 90 days.
End of study visit at 6 months.
1st interim analysis included 45 patients at Day 5.
Present data (at 2nd interim) includes total of 91 randomized patients with 30 days of follow-up.
  Inclusion criteria for the study population were:
  Males/females ≥40 to ≤80 years
  GOLD stages 2 to 4
  Smoking history at least 10 pack years
  Investigator defined COPD exacerbation
  Exclusion criteria for the study population were:
  Arterial blood pH <7.26 at randomization
  History or presence of clinically uncontrolled left heart failure
  Clinical or radiological evidence of pneumonia
  Long term Oxygen >15 hours a day
  History of clinically significant ECG abnormalities
  History or presence of impaired renal function
  Use of macrolide antibiotics within 48 hours of randomization
  Key efficacy endpoints:
  $FEV_1$ improvement from baseline at Day 5
  BORG Scores
  EXACT PRO:
    Recovery defined as reduction in EXACT score ≥9 points benchmarked against the maximum observed score (MOV: highest EXACT score using a 3-day rolling average) over the 14 day period following onset.
    Time to recovery
    Severity
      Maximum severity—highest exact score over 30 days
      Total severity—area under the curve from onset (i.e. Day 1) to recovery/Day 30 whichever comes first based on total exact score.
    Duration of exacerbation (days from onset to recovery/Day 30)
    Frequency of patients who recovered at Day 30
  Treatment failure:
    Patients who were treated with oral corticosteroids, admitted to hospital to COPD related symptoms, changed in antibiotic therapy relating to COPD, or in the attending physicians opinion needed treatment for a further exacerbation.

DEFINITIONS

Baseline is stable state and is reset every 4 weeks and last 7 days of week 4 are used to reset baseline value
Onset of an event is defined either as an increase in EXACT score of ≥12 points above the pt's mean baseline scores for 2 consecutive dates, with day 1 of the two days serving as Day 1 (onset of the event) OR an increase ≥9 points above the pt's mean baseline for 3 consecutive days, with day 1 of the 3 days serving as day 1 (onset) of the event.
Recovery is defined as improvement or decrease in EXACT score of at least 9 points from the maximum observed value during 14 days of an event that is sustained for 7 days using a 3 day rolling average.
Event duration is identified by: Onset, three day rolling average, maximum observe value, threshold for improvement and recovery.
Three day rolling average is used to account day to day variability in EXACT scores that can occur during an exacerbation (it is initiated on day 1 of onset and ends on Day 1 of recovery).
The results of the study are summarised in the following tables:

TABLE 1

Patient Disposition

| Disposition/Reason for discontinuation | Compound A (N = 31) n (%) | Placebo (N = 30) n (%) | Prednisone (N = 30) n (%) | All (N = 91) n (%) |
|---|---|---|---|---|
| Randomized | 31 (100) | 30 (100) | 30 (100) | 91 (100) |
| On-going | 24 (77.4) | 24 (80.0) | 21 (70.0) | 69 (75.8) |
| Discontinued | 0 (0.0) | 0 (0.0) | 4 (13.3) | 4 (4.4) |
| Adverse Events | 0 (0.0) | 0 (0.0) | 0 (0.0) | 0 (0.0) |
| Subject withdrew consent | 0 (0.0) | 0 (0.0) | 1 (3.3) | 1 (1.1) |
| Lost to follow-up | 0 (0.0) | 0 (0.0) | 1 (3.3) | 1 (1.1) |
| Death | 0 (0.0) | 0 (0.0) | 2 (6.7) | 2 (2.2) |

These results show patients treated with Compound A were not more likely than those receiving placebo or prednisone (an oral steroid) to discontinue participating in the study.

TABLE 2

Demographics and baseline characteristics

| Demographic | Compound A (N = 31) | Placebo (N = 30) | Prednisone (N = 30) | All (N = 91) |
|---|---|---|---|---|
| Age (years) Mean (SD) | 60.2 (8.58) | 60.7 (6.82) | 63.1 (7.98) | 61.3 (7.85) |
| Race Caucasian n (%) | 31 (100) | 30 (100) | 30 (100) | 91 (100) |
| Predominant Ethnicity | | | | |
| Hispanic/Latino n (%) | 1 (3.2) | 0 (0.0) | 1 (3.3) | 2 (2.2) |
| Other n (%) | 30 (96.8) | 30 (100) | 29 (96.7) | 2 (2.2) |
| Sex | | | | |
| Male n (%) | 23 (74.2) | 20 (66.7) | 26 (86.7) | 69 (75.8) |
| Female n (%) | 8 (25.8) | 10 (33.3) | 4 (13.3) | 69 (75.8) |

TABLE 2-continued

Demographics and baseline characteristics

| Demographic | Compound A (N = 31) | Placebo (N = 30) | Prednisone (N = 30) | All (N = 91) |
|---|---|---|---|---|
| | Baseline | | | |
| $FEV_1$ (L) Mean (SD)* | 1.336 (0.5511) | 1.402 (0.7084) | 1.186 (0.4817) | 1.308 (0.5885) |
| CV | 0.41 | 0.51 | 0.41 | 0.45 |
| FVC (L) Mean (SD) | 2.507 (0.8184) | 2.609 (0.9322) | 2.579 (0.7247) | 2.565 (0.8198) |

*Baseline difference in $FEV_1$ is not statistically significant (p-value = 0.1584).

These results show there are no differences in demography between groups (Prednisone group $FEV_1$ p>0.05 vs. Compound A and Placebo groups).

TABLE 3

Efficacy measured by $FEV_1$

| | Day 3 | | | Day 5 | | |
|---|---|---|---|---|---|---|
| Comparison | Difference | 95% CI | P-value | Difference | 95% CI | P-value |
| Compound A v placebo | 119.59 | (11.13, 228.04) | 0.016 | 46.56 | (−58.88, 152.00) | 0.191 |
| Compound A v prednisone | 102.28 | (−6.67, 211.22) | 0.033 | 109.15 | (3.23, 215.07) | 0.022 |

At day 5: No statistically significant improvement from baseline in FEV1 for Compound A cf. placebo (p 0.19), 46 ml improvement; Stat. Sig. vs. prednisone (p 0.02) although a failed positive control as prednisolone worse than placebo
At day 3: Significance reached between Compound A and placebo (p 0.016) and prednisone (p 0.03)

These results show patients receiving the treatment with Compound A showed greater improvement in $FEV_1$ versus placebo and prednisone at Day 3.

FEV1 change from baseline analysed with ANCOVA (analysis of variance) model for repeated measurements. Estimated between patient standard deviation—200 ml.

60% of the patients receiving the treatment with Compound A responded with >100 ml improvement on day 3. 27% of the patients receiving the treatment with the placebo responded with >100 ml improvement on day 3.

TABLE 4

Efficacy measured by $AUC_{[days\ 2-14]}$ in Borg CR 10 scores (adjusted for Day 1)

| Treatment | LS mean | Comparison | Difference LS mean | 95% CI | P-value |
|---|---|---|---|---|---|
| Compound A (N = 31) | 3.25 | Compound A - placebo | −0.23 | −0.65~0.19 | 0.1401 |
| Prednisone (N = 30) | 3.61 | Prednisone - placebo | 0.13 | −0.28~0.54 | 0.7378 |
| Placebo (N = 30) | 3.48 | Compound A - prednisone | −0.36 | −0.77~0.05 | 0.0418 |

These results show patients receiving the treatment with Compound A were on average less breathless over 14 days than patients who received treatment with prednisone LS is an abbreviation for least squares.

Treatment failure composite endpoint was defined as retreatment with antibiotics, oral steroids, death, hospitalization, or treatment in the opinion of the investigator indicating another exacerbation. Treatment failures for each treatment were as follows:

Compound A=0 patients
Placebo (standard of care+antibiotic alone)=5 patients
Prednisone=S patients Safety results are summarised in the following table:

TABLE 5

Most common adverse events by preferred term

| Number of subjects with AE Preferred term | Compound A (N = 31) n (%) | Placebo (N = 30) n (%) | Prednisone (N = 30) n (%) |
|---|---|---|---|
| Any AE | 8 (25.8) | 12 (40.0) | 12 (40.0) |
| COPD | 0 (0.0) | 5 (16.7) | 5 (16.7) |
| Headache | 1 (3.2) | 3 (10.0) | 3 (10.0) |
| Nausea | 0 (0.0) | 3 (10.0) | 2 (6.7) |
| Diarrhoea | 1 (3.2) | 2 (6.7) | 0 (0.0) |
| Dizziness | 2 (6.5) | 0 (0.0) | 0 (0.0) |
| Vertigo | 1 (3.2) | 1 (3.3) | 1 (3.3) |
| Nasopharyngitis | 1 (3.2) | 1 (3.3) | 1 (3.3) |
| Occult blood | 1 (3.2) | 1 (3.3) | 1 (3.3) |
| Abdominal pain upper | 1 (3.2) | 0 (0.0) | 1 (3.3) |

These results show Compound A administered as a single dose was safe and well tolerated. No COPD adverse events were observed with Compound A.

Initial hospitalization for COPD exacerbation at baseline was not recorded as a serious adverse event (SAE). Only subsequent admissions were recorded. Table 5 shows only adverse events that were experienced by at least 2 subjects in the study. No rash was noted. No unusual events or imbalances between treatment arms were noted.

The various features and embodiments of the present invention, referred to in individual sections above apply, as appropriate, to other sections, mutatis mutandis. Consequently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for the treatment of acute exacerbations of chronic obstructive pulmonary disease which comprises administering to a subject in need thereof an effective amount of 3-[5-amino-4-(3-cyanobenzoyl)-pyrazol-1-yl]-N-cyclopropyl-4-methylbenzamide or a pharmaceutically acceptable salt, hydrate or solvate thereof.

2. A method according to claim 1 wherein a single dose of 3-[5-amino-4-(3-cyano-benzoyl)-pyrazol-1-yl]-N-cyclopropyl-4-methylbenzamide or a pharmaceutically acceptable salt, hydrate or solvate thereof is administered.

3. A method according to claim 2 wherein the single dose comprises 50 to 100 mg of 3-[5-amino-4-(3-cyanobenzoyl)-pyrazol-1-yl]-N-cyclopropyl-4-methylbenzamide or a pharmaceutically acceptable salt, hydrate or solvate thereof.

4. A method according to claim 2 wherein the single dose comprises 60 to 90 mg of 3-[5-amino-4-(3-cyanobenzoyl)-pyrazol-1-yl]-N-cyclopropyl-4-methylbenzamide or a pharmaceutically acceptable salt, hydrate or solvate thereof.

5. A method according to claim 2 wherein the single dose comprises 75 mg of 3-[5-amino-4-(3-cyanobenzoyl)-pyrazol-1-yl]-N-cyclopropyl-4-methylbenzamide or a pharmaceutically acceptable salt, hydrate or solvate thereof.

6. A method according to claim 2 wherein the single dose comprises 75 mg of 3-[5-amino-4-(3-cyanobenzoyl)-pyrazol-1-yl]-N-cyclopropyl-4-methylbenzamide in its free form.

7. A method according to claim 1 wherein said 3-[5-amino-4-(3-cyano-benzoyl)-pyrazol-1-yl]-N-cyclopropyl-4-methylbenzamide or a pharmaceutically acceptable salt thereof is administered to said subject.

8. A method according to claim 7 wherein 50 to 100 mg of 3-[5-amino-4-(3-cyanobenzoyl)-pyrazol-1-yl]-N-cyclopropyl-4-methylbenzamide or a pharmaceutically acceptable salt thereof is administered to said subject.

9. A method according to claim 8 wherein 60 to 90 mg of 3-[5-amino-4-(3-cyanobenzoyl)-pyrazol-1-yl]-N-cyclopropyl-4-methylbenzamide or a pharmaceutically acceptable salt-thereof is administered to said subject.

10. A method according to claim 9 wherein 75 mg of 3-[5-amino-4-(3-cyanobenzoyl)-pyrazol-1-yl]-N-cyclopropyl-4-methylbenzamide or a pharmaceutically acceptable salt thereof is administered to said subject.

11. A method according to claim 8 wherein 3-[5-amino-4-(3-cyanobenzoyl)-pyrazol-1-yl]-N-cyclopropyl-4-methylbenzamide is in its free form.

* * * * *